United States Patent
Shiraki

(10) Patent No.: US 7,498,467 B2
(45) Date of Patent: Mar. 3, 2009

(54) ANTIOXIDANT AND BISAMINOPHENOL DERIVATIVE

(75) Inventor: Yasushi Shiraki, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 12/039,804

(22) Filed: Feb. 29, 2008

(65) Prior Publication Data

US 2008/0161608 A1 Jul. 3, 2008

Related U.S. Application Data

(62) Division of application No. 10/551,451, filed as application No. PCT/JP2004/004608 on Mar. 31, 2004.

(30) Foreign Application Priority Data

Apr. 2, 2003 (JP) ............................. 2003-099104
Dec. 9, 2003 (JP) ............................. 2003-410630

(51) Int. Cl.
*C07C 215/54* (2006.01)
(52) U.S. Cl. ..................................... 564/355
(58) Field of Classification Search ........................ None
See application file for complete search history.

(56) References Cited

U.S. PATENT DOCUMENTS

| 2,275,311 A | 3/1942 | Pedersen et al. |
| 3,033,662 A | 5/1962 | Thompson |
| 3,149,933 A | 9/1964 | Ley et al. |
| 5,114,826 A | 5/1992 | Kwong et al. |
| 5,700,879 A | 12/1997 | Yamamoto et al. |
| 6,498,191 B2 | 12/2002 | Ghosh et al. |

FOREIGN PATENT DOCUMENTS

| GB | 1246645 | 9/1971 |
| JP | 51-58482 | 5/1976 |
| JP | 63-135437 | 6/1988 |
| SU | 523 080 | 2/1974 |
| SU | 569 559 | 9/1977 |

*Primary Examiner*—Samuel A Barts
(74) *Attorney, Agent, or Firm*—Oblon, Spivak, McClelland, Maier & Neustadt, P.C.

(57) ABSTRACT

The present invention provides antioxidants made of an aromatic hydroxyamine derivative having a structure represented by the general formula (I):

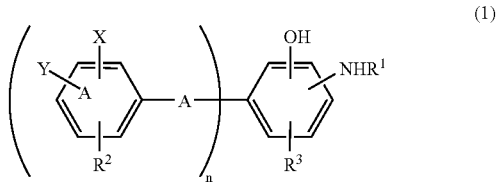

wherein $R^1$, $R^2$ and $R^3$ are each independently a hydrogen atom or an alkyl group having 1 to 20 carbon atoms; X is a hydrogen atom or an OH group; Y is a hydrogen atom or an $NHR^1$ group; A is a direct bond, —O—, —NH—, —$SO_2$—, —$CH_2$— or —$C(CH_3)_2$—, and when an OH group and an $NHR^1$ group are introduced to a unilateral benzene ring, these groups are respectively bonded to adjacent positions of the benzene ring; and n is 0 or 1 with the proviso that when n is 0, $R^1$ is not a hydrogen atom, as well as bisaminophenol derivatives represented by the above general formula (I) wherein n is 1; $R^2$ and $R^3$ are each a hydrogen atom; X is an OH group; Y is an $NHR^1$ group; A is —$C(CH_3)_2$—; and $R^1$ is isopropyl, isobutyl or isohexyl. The aromatic hydroxyamine derivatives having a structure represented by the general formula (I), in particular, the bisaminophenol derivatives as novel substances, exhibit an excellent oxidation-inhibiting property, and are usable as antioxidants or polymerization inhibitors.

3 Claims, No Drawings

ANTIOXIDANT AND BISAMINOPHENOL DERIVATIVE

REFERENCE TO PRIOR APPLICATIONS

This application is a Divisional application of U.S. application Ser. No. 10/551,451, filed Sep. 29, 2005, now pending; which is National Stage application of PCT/JP04/04608, filed Mar. 31, 2004 and claims priority to Japanese patent applications 2003-099104, filed Apr. 2, 2003, and 2003-410630, filed Dec. 9, 2003.

TECHNICAL FIELD

The present invention relates to novel antioxidants and aromatic hydroxyamine derivatives, and more particularly to antioxidants made of aromatic hydroxyamine derivatives containing a hydroxyl group and an amino or monoalkylamino group respectively bonded to adjacent positions of an aromatic ring thereof which exhibit an excellent oxidation-inhibiting effect and are suitably used for plastics, rubbers, petroleum products, etc., as well as bisaminophenol derivatives.

BACKGROUND ART

Hitherto, antioxidants have been extensively used in various applications such as plastic products, rubber products, petroleum products (such as lubricating oils) and food. The antioxidants are mainly used for the purpose of inhibiting these products from suffering from undesirable change due to oxygen.

There are conventionally known various kinds of antioxidants. Among these antioxidants, radical chain inhibitors (primary antioxidants) serve for capturing radicals produced upon autoxidation, inhibiting production of the radicals and cutting the radical chain, and are mainly made of hindered phenol-based compounds such as typically 2,6-di-tert-butyl-p-cresol or amine-based compounds such as typically N,N'-diphenyl-p-phenylenediamine. Also, among the antioxidants, peroxide decomposing agents (secondary antioxidants) serve for decomposing peroxides produced upon autoxidation into inert compounds to thereby prevent contribution of the peroxides to chain reaction, and are most frequently made of sulfur-based or phosphorus-based compounds. It is known that when the peroxide decomposing agents are used in combination with the above radical chain inhibitors, a good synergistic effect can be attained.

In the primary antioxidants, in general, the amine-based compounds exhibit a higher oxidation-inhibiting property as compared to the phenol-based compounds. However, since oxidation products produced using the amine-based compounds tend to have a deep color, the use of the amine-based compounds must be limited to applications such as rubber products in which coloration of products causes no significant problems.

As typical amine-based antioxidants used for production of rubber products, there are known N,N'-diphenyl-p-phenylenediamine, N-isopropyl-N'-phenyl-p-phenylenediamine (so-called "3C"), N-(1,3-dimethylbutyl)-N'-phenyl-p-phenylenediamine (so-called "6C"), etc. In addition, as the amine-based antioxidants, there are also known high-molecular diamines produced from a p-aminophenol derivative and aniline, etc. (JP 53-103429A).

On the other hand, as the typical phenol-based antioxidants, there are known 2,6-di-tert-butyl-p-cresol as a mononuclear compound (so-called "BHT"), 2,2'-methylenebis(4-methyl-6-tert-butylphenol) as a binuclear compound (so-called "2246"), tetrakis[methylene-3-(3,5-di-tert-butyl-4-hydroxyphenyl)propionate]methane as a tetranuclear compound (tradename "Irganox 1010" available from Ciba Specialty Co., Ltd.), etc.

These antioxidants have been required to exhibit a high oxidation inhibiting property even when they are added in a small amount. Further, high-molecular antioxidants are more excellent in view of volatility, migration, extractability, etc., than low-molecular antioxidants. Therefore, in particular in the application field of plastic products, the high-molecular antioxidants tend to be more frequently used.

Meanwhile, aromatic binuclear compounds in which a hydroxyl group and an amino group are respectively bonded to adjacent positions of an aromatic ring thereof have been positively studied as raw materials for polybenzoxazole having excellent heat resistance and electrical insulating property. However, at present, there is almost unknown an oxidation inhibiting property of the aromatic binuclear compounds.

DISCLOSURE OF THE INVENTION

Under these circumstances, an object of the present invention is to provide a novel antioxidant which has a high oxidation-inhibiting property and is suitably used in plastics, rubbers, petroleum products, etc.

As a result of extensive researches for accomplishing the above object, the inventors have found that aminophenol derivatives in which a hydroxyl group and an amino group are respectively bonded to adjacent ortho positions of an aromatic ring thereof exhibit an excellent oxidation-inhibiting property and are effective as a polymerization inhibitor, and in particular, specific bisaminophenol derivatives as novel substances are extremely excellent in oxidation-inhibiting property. The present invention has been accomplished on the basis of the above finding.

Thus, the present invention provides:

(1) An antioxidant made of an aromatic hydroxyamine derivative having a structure represented by the general formula (I):

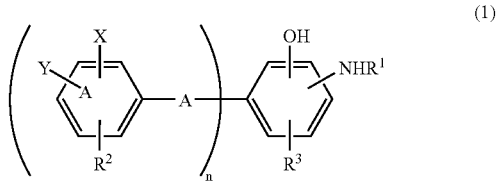

(1)

wherein $R^1$, $R^2$ and $R^3$ are each independently a hydrogen atom or an alkyl group having 1 to 20 carbon atoms; X is a hydrogen atom or an OH group; Y is a hydrogen atom or an $NHR^1$ group; A is a direct bond, —O—, —NH—, —$SO_2$—, —$CH_2$— or —$C(CH_3)_2$—, and when an OH group and an $NHR^1$ group are introduced to a unilateral benzene ring, these groups are respectively bonded to adjacent positions of the benzene ring; and n is 0 or 1 with the proviso that when n is 0, $R^1$ is not a hydrogen atom;

(2) the antioxidant according to the above aspect (1), wherein the antioxidant is used for plastics, rubbers or petroleum products; and (3) a bisaminophenol derivative represented by the general formula (I):

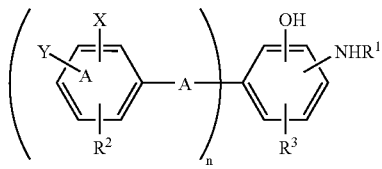

wherein n is 1; $R^2$ and $R^3$ are each a hydrogen atom; X is an OH group; Y is an $NHR^1$ group; A is —$C(CH_3)_2$—; and $R^1$ is isopropyl group, isobutyl group or isohexyl group.

BEST MODE FOR CARRYING OUT THE INVENTION

The antioxidant of the present invention is made of an aromatic hydroxyamine derivative having a structure represented by the general formula (I):

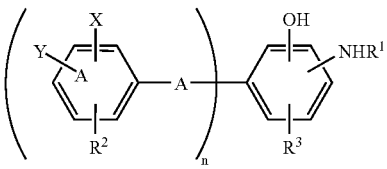

In the above general formula (I), $R^1$, $R^2$ and $R^3$ are each independently a hydrogen atom or an alkyl group having 1 to 20 carbon atoms; X is a hydrogen atom or an OH group; and Y is a hydrogen atom or an $NHR^1$ group. Here, the alkyl group having 1 to 20 carbon atoms as $R^1$, $R^2$ and $R^3$ may be either linear, branched or cyclic. Examples of the alkyl group include methyl, ethyl, n-propyl, isopropyl, various butyl groups, various pentyl groups, various hexyl groups, various octyl groups, various decyl groups, various dodecyl groups, various tetradecyl groups, various hexadecyl groups, various octadecyl groups, various eicosyl groups, cyclopentyl, cyclohexyl, methylcyclohexyl, cyclopentylmethyl and cyclohexylmethyl. Among these alkyl groups, preferred are alkyl groups having 1 to 10 carbon atoms.

The amino groups represented by $NHR^1$ are preferably secondary amines and more preferably those amines substituted with an alkyl group having 3 to 10 carbon atoms, i.e., from propyl to decyl. Further, if $R^2$ and $R^3$ are respectively an alkyl group, the resultant compound exhibits a still higher oxidation-inhibiting property.

A is a direct bond, —O—, —NH—, —$SO_2$—, —$CH_2$— or —$C(CH_3)_2$—, and when an OH group and an $NHR^1$ group are introduced to a unilateral benzene ring, these groups are respectively bonded to adjacent positions of the benzene ring. The symbol n is 0 or 1 with the proviso that when n is 0, $R^1$ is not a hydrogen atom.

Examples of the compounds represented by the general formula (I) wherein n is 0 include 2-(methylamino)phenol, 2-(ethylamino)phenol, 2-(n-propylamino)phenol, 2-(isopropylamino)phenol, 2-(n-butylamino)phenol, 2-(isobutylamino)phenol, 2-(sec-butylamino)phenol, 2-(n- or isopentylamino)phenol, 2-(1-methylpentylamino)phenol, 2-(n- or isohexylamino)phenol, 2-(n- or isoheptylamino)phenol, 2-(n- or isooctylamino)phenol, 2-(n- or isononylamino)phenol, 2-(n- or isodecylamino)phenol and 2-(isopropylamino)-4-tert-butylphenol.

Examples of the compounds represented by the general formula (I) wherein n is 1 include compounds represented by the following general formula (I-a) to (I-d):

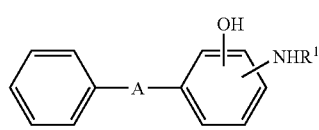

(I-a)

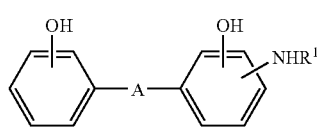

(I-b)

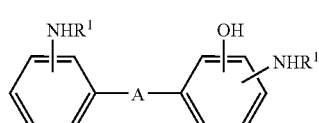

(I-c)

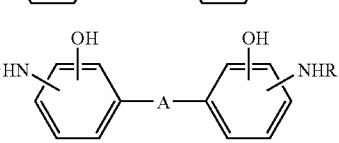

(I-d)

wherein $R^1$ is a hydrogen atom or an alkyl group having 1 to 20 carbon atoms; and A has the same meaning as defined above, and when an OH group and an $NHR^1$ group are introduced to a unilateral benzene ring, these groups are respectively bonded to adjacent positions of the benzene ring.

Examples of the compounds represented by the general formula (I-a) include 3-amino-4-hydroxydiphenyl, 3-alkylamino-4-hydroxydiphenyls, 4-amino-3-hydroxydiphenyl, 4-alkylamino-3-hydroxydiphenyls, 2-amino-3-hydroxydiphenyl, 2-alkylamino-3-hydroxydiphenyls, 3-amino-2-hydroxydiphenyl, 3-alkylamino-2-hydroxydiphenyls, 3-amino-4-hydroxydiphenyl ether, 3-alkylamino-4-hydroxydiphenyl ethers, 4-amino-3-hydroxydiphenyl ether, 4-alkylamino-3-hydroxydiphenyl ethers, 2-amino-3-hydroxydiphenyl ether, 2-alkylamino-3-hydroxydiphenyl ethers, 3-amino-2-hydroxydiphenyl ether, 3-alkylamino-2-hydroxydiphenyl ethers, 3-amino-4-hydroxydiphenyl amine, 3-alkylamino-4-hydroxydiphenyl amines, 4-amino-3-hydroxydiphenylamine, 4-alkylamino-3-hydroxydiphenyl amines, 2-amino-3-hydroxydiphenylamine, 2-alkylamino-3-hydroxydiphenyl amines, 3-amino-2-hydroxydiphenylamine, 3-alkylamino-2-hydroxydiphenyl amines, 3-amino-4-hydroxydiphenyl sulfone, 3-alkylamino-4-hydroxydiphenyl sulfones, 4-amino-3-hydroxydiphenyl sulfone, 4-alkylamino-3-hydroxydiphenyl sulfones, 2-amino-3-hydroxydiphenyl sulfone, 2-alkylamino-3-hydroxydiphenyl sulfones, 3-amino-2-hydroxydiphenyl sulfone, 3-alkylamino-2-hydroxydiphenyl sulfones, 3-amino-4-hydroxydiphenyl methane, 3-alkylamino-4-hydroxydiphenyl methanes, 4-amino-3-hydroxydiphenyl methane, 4-alkylamino-3-hydroxydiphenyl methanes, 2-amino-3-hydroxydiphenyl methane, 2-alkylamino-3-hydroxydiphenyl methanes, 3-amino-2-hydroxydiphenyl methane, 3-alkylamino-2-hydroxydiphenyl methanes, 2-phenyl-2-(3-amino-4-hydroxyphenyl)propane, 2-phenyl-2-(3-alkylamino-4-hydroxyphenyl)propanes, 2-phenyl-2-(4-amino-3-hydroxyphenyl)propane, 2-phenyl-2-(4- alkylamino-3-hydroxyphenyl)propanes, 2-phenyl-2-(2-amino-3-hydroxyphenyl)propane, 2-phenyl-2-(2-alkylamino-3-hydroxyphenyl)propanes, 2-phenyl-2-(3-amino-2-hydroxyphenyl)propane and 2-phenyl-2-(3-alkylamino-2-hydroxyphenyl)propanes.

Examples of the compounds represented by the general formula (1-b) include 3-amino-3',4-dihydroxydiphenyl, 3-alkylamino-3',4-dihydroxydiphenyls, 3-amino-4,4'-dihydroxydiphenyl, 3-alkylamino-4,4'-dihydroxydiphenyls, 4-amino-3,3'-dihydroxydiphenyl, 4-alkylamino-3,3'-dihydroxydiphenyls, 4-amino-3,4'-dihydroxydiphenyl, 4-alkylamino-3,4'-dihydroxydiphenyls, 3-amino-3,4'-dihydroxydiphenyl ether, 3-alkylamino-3,4'-dihydroxydiphenyl ethers, 3-amino-4,4'-dihydroxydiphenyl ether, 3-alkylamino-4,4'-dihydroxydiphenyl ethers, 4-amino-3,3'-dihydroxydiphenyl ether, 4-alkylamino-3,3'-dihydroxydiphenyl ethers, 4-amino-3,4'-dihydroxydiphenyl ether, 4-alkylamino-3,4'-dihydroxydiphenyl ethers, 3-amino-3',4-dihydroxydiphenyl amine, 3-alkylamino-3',4-dihydroxydiphenyl amines, 3-amino-4,4'-dihydroxydiphenyl amine, 3-alkylamino-4,4'-dihydroxydiphenyl amines, 4-amino-3,3'-dihydroxydiphenyl amine, 4-alkylamino-3,3'-dihydroxydiphenyl amines, 4-amino-3,4'-dihydroxydiphenyl amine, 4-alkylamino-3,4'-dihydroxydiphenyl amines, 3-amino-3',4-dihydroxydiphenyl sulfone, 3-alkylamino-3',4-dihydroxydiphenyl sulfones, 3-amino-4,4'-dihydroxydiphenyl sulfone, 3-alkylamino-4,4'-dihydroxydiphenyl sulfones, 4-amino-3,3'-dihydroxydiphenyl sulfone, 4-alkylamino-3,3'-dihydroxydiphenyl sulfones, 4-amino-3,4'-dihydroxydiphenyl sulfone, 4-alkylamino-3,4'-dihydroxydiphenyl sulfones, 3-amino-3',4-dihydroxydiphenyl methane, 3-alkylamino-3',4-dihydroxydiphenyl methanes, 3-amino-4,4'-dihydroxydiphenyl methane, 3-alkylamino-4,4'-dihydroxydiphenyl methanes, 4-amino-3,3'-dihydroxydiphenyl methane, 4-alkylamino-3,3'-dihydroxydiphenyl methanes, 4-amino-3,4'-dihydroxydiphenyl methane, 4-alkylamino-3,4'-dihydroxydiphenyl methanes, 2-(3-amino-4-hydroxyphenyl)-2-(3'-hydroxyphenyl)propane, 2-(3-alkylamino-4-hydroxyphenyl)-2-(3'-hydroxyphenyl)propanes, 2-(3-amino-4-hydroxyphenyl)-2-(4'-hydroxyphenyl)propane, 2-(3-alkylamino-4-hydroxyphenyl)-2-(4'-hydroxyphenyl)propanes, 2-(4-amino-3-hydroxyphenyl)-2-(3'-hydroxyphenyl)propane, 2-(4-alkylamino-3-hydroxyphenyl)-2-(3'-hydroxyphenyl)propanes, 2-(4-amino-3-hydroxyphenyl)-2-(4'-hydroxyphenyl)propane and 2-(4-alkylamino-3-hydroxyphenyl)-2-(4'-hydroxyphenyl)propanes.

Examples of the compounds represented by the general formula (I-c) include 3,3'-diamino-4-hydroxydiphenyl, 3,3'-di(alkylamino)-4-hydroxydiphenyls, 3,4'-diamino-4-hydroxydiphenyl, 3,4'-di(alkylamino)-4-hydroxydiphenyls, 3',4-diamino-3-hydroxydiphenyl, 3',4-di(alkylamino)-3-hydroxydiphenyls, 4,4'-diamino-3-hydroxydiphenyl, 4,4'-di(alkylamino)-3-hydroxydiphenyls, 3,3'-diamino-4-hydroxydiphenyl ether, 3,3'-di(alkylamino)-4-hydroxydiphenyl ethers, 3,4'-diamino-4-hydroxydiphenyl ether, 3,4'-di(alkylamino)-4-hydroxydiphenyl ethers, 3',4-diamino-3-hydroxydiphenyl ether, 3',4-di(alkylamino)-3-hydroxydiphenyl ethers, 4,4'-diamino-3-hydroxydiphenyl ether, 4,4'-di(alkylamino)-3-hydroxydiphenyl ethers, 3,3'-diamino-4-hydroxydiphenyl amine, 3,3'-di(alkylamino)-4-hydroxydiphenyl amines, 3,4'-diamino-4-hydroxydiphenyl amine, 3,4'-di(alkylamino)-4-hydroxydiphenyl amines, 3',4-diamino-3-hydroxydiphenyl amine, 3',4-di(alkylamino)-3-hydroxydiphenyl amine, 4,4'-diamino-3-hydroxydiphenyl amines, 4,4'-di(alkylamino)-3-hydroxydiphenyl amines, 3,3'-diamino-4-hydroxydiphenyl sulfone, 3,3'-di(alkylamino)-4-hydroxydiphenyl sulfones, 3,4'-diamino-4-hydroxydiphenyl sulfone, 3,4'-di(alkylamino)-4-hydroxydiphenyl sulfones, 3',4-diamino-3-hydroxydiphenyl sulfone, 3',4-di(alkylamino)-3-hydroxydiphenyl sulfones, 4,4'-diamino-3-hydroxydiphenyl sulfone, 4,4'-di(alkylamino)-3-hydroxydiphenyl sulfones, 3,3'-diamino-4-hydroxydiphenyl methane, 3,3'-di(alkylamino)-4-hydroxydiphenyl methanes, 3,4'-diamino-4-hydroxydiphenyl methane, 3,4'-di(alkylamino)-4-hydroxydiphenyl methanes, 3',4-diamino-3-hydroxydiphenyl methane, 3',4-di(alkylamino)-3-hydroxydiphenyl methanes, 4,4'-diamino-3-hydroxydiphenyl methane, 4,4'-di(alkylamino)-3-hydroxydiphenyl methanes, 2-(3'-aminophenyl)-2-(3-amino-4-hydroxyphenyl)propane, 2-(3'-alkylaminophenyl)-2-(3-alkylamino-4-hydroxyphenyl)propanes, 2-(4'-aminophenyl)-2-(3-amino-4-hydroxyphenyl)propane, 2-(4'-alkylaminophenyl)-2-(3-alkylamino-4-hydroxyphenyl)propanes, 2-(3'-aminophenyl)-2-(4-amino-3-hydroxyphenyl)propane, 2-(3'-alkylaminophenyl)-2-(4-alkylamino-3-hydroxyphenyl)propanes, 2-(4'-aminophenyl)-2-(4-amino-3-hydroxyphenyl)propane and 2-(4'-alkylaminophenyl)-2-(4-alkylamino-3-hydroxyphenyl)propanes.

Examples of the compounds represented by the general formula (I-d) include 3,3'-diamino-4,4'-dihydroxydiphenyl, 3,3'-di(alkylamino)-4,4'-dihydroxydiphenyls, 4,4'-diamino-3,3'-dihydroxydiphenyl, 4,4'-di(alkylamino)-3,3'-dihydroxydiphenyls, 2,2'-diamino-3,3'-dihydroxydiphenyl, 2,2'-di(alkylamino)-3,3'-dihydroxydiphenyls, 3,3'-diamino-2,2'-dihydroxydiphenyl, 3,3'-di(alkylamino)-2,2'-dihydroxydiphenyls, 3,3'-diamino-4,4'-dihydroxydiphenyl ether, 3,3'-di(alkylamino)-4,4'-dihydroxydiphenyl ethers, 4,4'-diamino-3,3'-dihydroxydiphenyl ether, 4,4'-di(alkylamino)-3,3'-dihydroxydiphenyl ethers, 2,2'-diamino-3,3'-dihydroxydiphenyl ether, 2,2'-di(alkylamino)-3,3'-dihydroxydiphenyl ethers, 3,3'-diamino-2,2'-dihydroxydiphenyl ether, 3,3'-di(alkylamino)-2,2'-dihydroxydiphenyl ethers, 3,3'-diamino-4,4'-dihydroxydiphenyl amine, 3,3'-di(alkylamino)-4,4'-dihydroxydiphenyl amines, 4,4'-diamino-3,3'-dihydroxydiphenyl amine, 4,4'-di(alkylamino)-3,3'-dihydroxydiphenyl amines, 2,2'-diamino-3,3'-dihydroxydiphenyl amine, 2,2'-di(alkylamino)-3,3'-dihydroxydiphenyl amines, 3,3'-diamino-2,2'-dihydroxydiphenyl amine, 3,3'-di(alkylamino)-2,2'-dihydroxydiphenyl amines, 3,3'-diamino-4,4'-dihydroxydiphenyl sulfone, 3,3'-di(alkylamino)-4,4'-dihydroxydiphenyl sulfones, 4,4'-diamino-3,3'-dihydroxydiphenyl sulfone, 4,4'-di(alkylamino)-3,3'-dihydroxydiphenyl sulfones, 2,2'-diamino-3,3'-dihydroxydiphenyl sulfone, 2,2'-di(alkylamino)-3,3'-dihydroxydiphenyl sulfones, 3,3'-diamino-2,2'-dihydroxydiphenyl sulfone, 3,3'-di(alkylamino)-2,2'-dihydroxydiphenyl sulfones, 3,3'-diamino-4,4'-dihydroxydiphenyl methane, 3,3'-di(alkylamino)-4,4'-dihydroxydiphenyl methanes, 4,4'-diamino-3,3'-dihydroxydiphenyl methane, 4,4'-di(alkylamino)-3,3'-dihydroxydiphenyl methanes, 2,2'-diamino-3,3'-dihydroxydiphenyl methane, 2,2'-di(alkylamino)-3,3'-dihydroxydiphenyl methanes, 3,3'-diamino-2,2'-dihydroxydiphenyl methane, 3,3'-di(alkylamino)-2,2'-dihydroxydiphenyl methanes, 2,2-bis(3-amino-4-hydroxyphenyl)propane, 2,2-bis[3-(alkylamino)-4-hydroxyphenyl]propanes, 2,2-bis(4-amino-3-hydroxyphenyl)propane, 2,2-bis[4-(alkylamino)-3-hydroxyphenyl]propanes, 2,2-bis(2-amino-3-hydroxyphenyl)propane, 2,2-bis[2-(alkylamino)-3-hydroxyphenyl]propanes, 2,2-bis(3-amino-2-hydroxyphenyl)propane and 2,2-bis[3-(alkylamino)-2-hydroxyphenyl]propanes.

Examples of the alkyl group in the alkylamino group of the above-exemplified compounds include methyl, ethyl, n-propyl, isopropyl, n-butyl, isobutyl, sec-butyl, n- or isopentyl, n- or isohexyl, n- or isoheptyl, n- or isooctyl and n- or isodecyl.

Next, the process for production of the aromatic hydroxyamine derivatives is explained.

The compounds represented by the general formula (I-2) which correspond to those compounds represented by the general formula (I) wherein $R^1$ is an alkyl group having 1 to 20 carbon atoms may be produced, for example, according to the following reaction formula (a):

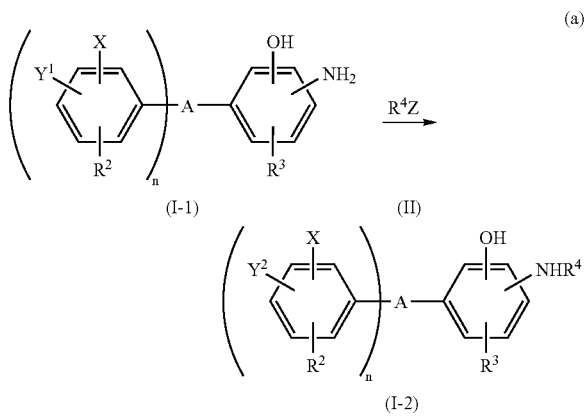

wherein $R^4$ is an alkyl group having 1 to 20 carbon atoms; $Y^1$ is a hydrogen atom or an $NH_2$ group; $Y^2$ is a hydrogen atom or —$NHR^4$; Z is a halogen atom or an oxygen atom; $R^2$, $R^3$, X, A and n have the same meaning as defined above, and when an OH group and an $NH_2$ or $NHR^4$ group are introduced to a unilateral benzene ring, these groups are respectively bonded to adjacent positions of the benzene ring.

When an aromatic hydroxyamine derivative represented by the general formula (I-1) and $R^4Z$ are reacted with each other in substantially stoichiometric amounts in the presence of an appropriate solvent, for example, dimethylformamide under the following conditions, the aromatic hydroxyamine derivative represented by the general formula (I-2) in the form of an N-monoalkyl-substituted compound of the above aromatic hydroxyamine derivative is produced.

In the case where Z is a halogen atom, namely $R^4Z$ is an alkyl halide (for example, alkyl chloride, alkyl bromide, alkyl iodide, etc.), the reaction is conducted at a temperature of usually from 0 to 100° C. and preferably from 10 to 60° C. in the presence of a hydrogen halide capturing agent.

On the other hand, in the case where Z is an oxygen atom, namely $R^4Z$ is a ketone (for example, acetone, methyl ethyl ketone, hexanone, etc.), the reaction is conducted at a temperature of usually from 100 to 200° C. and preferably from 130 to 180° C. in the presence of a dehydrating agent under a hydrogen gas flow. The use of the ketone as $R^4Z$ makes it possible to obtain the aimed compound at a high yield as described in Examples hereinlater.

As the hydrogen halide capturing agent, there may be used inorganic basic compounds and organic basic compounds. Examples of the inorganic basic compounds include sodium hydroxide, potassium hydroxide, sodium carbonate, potassium carbonate, sodium hydrogencarbonate and potassium hydrogencarbonate. Examples of the organic basic compounds include tertiary amines such as triethylamine, pyridine and picoline.

Examples of the dehydrating agent include magnesium sulfate and diphosphorus pentaoxide.

Also, the bisaminophenol compound represented by the general formula (I-1-a) may be produced, for example, according to the following reaction formula (b):

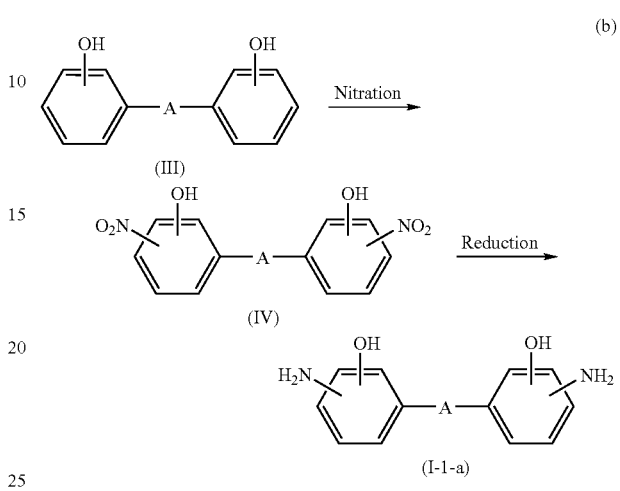

wherein an OH group and an $NO_2$ group introduced into the same benzene ring in the general formula (IV) as well as an OH group and an $NH_2$ group introduced into the same benzene ring in the general formula (I-1-a) are respectively bonded to adjacent positions of the benzene ring; and A has the same meaning as defined above.

The bisphenol compound represented by the general formula (III) is nitrated with a nitrating agent such as nitric acid at a temperature of usually from −30 to 30° C. and preferably from 0° C. to room temperature for about 1 to 10 h in an appropriate solvent inert to the nitration reaction, for example, dichloromethane, thereby obtaining a bisnitrophenol compound represented by the general formula (IV). In the nitration reaction, since the hydroxyl group acts as an electron donating group, the nitro groups are usually introduced into o- and p-positions relative to the hydroxyl group. Therefore, when the divalent A group is bonded to the p-position relative to the hydroxyl group, the o-nitrophenol compound is produced at a very high selectivity in the nitration reaction.

Next, the thus-obtained bisnitrophenol compound (IV) is subjected to reduction reaction with a reducing agent such as a hydrogen gas in an appropriate solvent, for example, an alcohol-based solvent in the presence of a reducing catalyst. As the reducing catalyst, there may be used those catalysts obtained by supporting metal catalysts such as palladium/carbon (Pd/C), nickel and platinum on a carrier such as alumina, silica gel and zeolite. The reduction treatment may be usually conducted under a pressure of 0.1 to 10 MPa at a temperature ranging from ordinary temperature to about 150° C. for about 1 to 20 h, thereby obtaining the bisaminophenol compound represented by the general formula (I-1-a).

The aromatic hydroxyamine derivative represented by the general formula (I) exhibits a high oxidation-inhibiting property, and can be used not only as an antioxidant for plastic products, rubber products, petroleum products (such as lubricating oil and fuel oil), etc., but also as a polymerization inhibitor.

Meanwhile, among the aromatic hydroxylamine derivatives having a structure represented by the general formula (I), the bisaminophenol derivatives represented by the general formula (I) wherein n is 1; $R^2$ and $R^3$ are each a hydrogen atom; X is an OH group; Y is an $NHR^1$ group; A is —C$(CH_3)_2$—; and $R^1$ is isopropyl, isobutyl or isohexyl, are novel substances, and exhibit a more excellent oxidation-inhibiting property as shown in Examples 15 to 17 below.

The present invention will be described in more detail by reference to the following examples. However, it should be noted that these examples are only illustrative and not intended to limit the invention thereto.

Meanwhile, in the following examples and comparative examples, the oxidation-inhibiting property was determined from an oxygen absorption initiation time measured by the following method.

Method for Measuring Oxidation-Inhibiting Property:

Into 50 g of tetralin were added 0.05 mmol of a sample and 0.02 g (0.12 mmol) of AIBN (azobisisobutyronitrile) as a polymerization initiator, and the resultant mixture was stirred at room temperature and completely dissolved. The oxidative stability of the obtained solution was measured by an oxidative stability tester according to JIS K2287. Meanwhile, the oxidative stability test was conducted under an oxygen pressure of 0.7 MPa at 100° C., and the time at which the oxygen pressure was reduced by 5% was determined as an oxidation absorption initiation time.

EXAMPLE 1

Synthesis of 2-(isopropylamino)phenol

Into a 100 mL flask purged with nitrogen were added 12 g (109.92 mmol) of o-aminophenol and 60 mL of dimethylformamide (DMF), and the resultant mixture was stirred at room temperature and dissolved. Then, the obtained solution was mixed with 22.4 g (132 mmol) of 2-iodopropane such (molar ratio of 2-iodopropane to o-aminophenol: 1.2), and further with 11.4 g (114 mmol) of potassium hydrogencarbonate ($KHCO_3$) as a catalyst, and the resultant mixture was stirred at room temperature for 5 h. After conducting the reaction for 5 h, 50 mL of water was added to the reaction solution to terminate the reaction.

As a result, it was confirmed that the rate of conversion of o-aminophenol was 72%, and the selectivity to the N-monoalkylated compound as produced (molar ratio of the monoalkylated compound to a sum of the mono- and di-alkylated compounds) was 73%.

The resultant reaction solution containing water was extracted with 50 mL of ethyl acetate three times, and the thus extracted organic layer was dried with $MgSO_4$. Thereafter, the dried organic layer was concentrated using an evaporator, and then hexane was added to the concentrated solution to crystallize unreacted o-aminophenol. The resultant solution was subjected to suction filtration to remove the crystals therefrom, and the filtrate thus separated was mixed with water to crystallize 2-(isopropylamino)phenol as the aimed reaction product. As a result, it was confirmed that the purity of 2-(isopropylamino)phenol as produced was 96.4%, and the oxygen absorption initiation time as an index of determining an oxidation-inhibiting property thereof was 370 min.

EXAMPLE 2

Synthesis of 2-(isopropylamino)phenol

The same procedure as in Example 1 was repeated except that the molar ratio of 2-iodopropane to o-aminophenol was changed to 1.0, the 2-iodopropane was dropped over 3 h, and then the reaction mixture was stirred at room temperature for 2 h.

As a result, it was confirmed that the rate of conversion of o-aminophenol was 58%, the selectivity to the N-monoalkylated compound was 99%, and the oxygen absorption initiation time as an index of determining an oxidation-inhibiting property thereof was 370 min.

EXAMPLE 3

Synthesis of 2-(isopropylamino)phenol

Into a 300 mL autoclave were charged 12 g (109.92 mmol) of o-aminophenol, 100 mL (79 g; 1.4 mol) of acetone, 0.6 g of Pd/C (Pd content: 5% by mass) and 30 g of $MgSO_4$, and the contents of the autoclave were heated at 100° C. while stirring under a hydrogen pressure of 1.0 MPa. After the elapse of 1 h, the hydrogen absorption was ceased, and the reaction was terminated. The resultant reaction solution was subjected to suction filtration to remove Pd/C and $MgSO_4$ therefrom, and the filtrate thus separated was concentrated and then mixed with water to crystallize a reaction product. The thus obtained reaction product was dried to obtain 2-(isopropylamino)phenol. As a result, it was confirmed that the yield of 2-(isopropylamino)phenol was 93%, and the oxygen absorption initiation time as an index of determining an oxidation-inhibiting property thereof was 370 min.

EXAMPLE 4

Synthesis of 2-(sec-butylamino)phenol

The same procedure as in Example 1 was repeated except for using 2-iodobutane in place of 2-iodopropane, to conduct the reaction. As a result, it was confirmed that the rate of conversion of o-aminophenol was 48%, and the selectivity to the N-monoalkylated compound was 100%.

After completion of the reaction, hexane was added to the concentrated ethyl acetate solution, followed by stirring the solution. The reaction solution was subjected to suction filtration to separate the solution into a solid (unreacted o-aminophenol) and a filtrate. A hexane layer as the filtrate was washed with water to further remove the unreacted o-aminophenol therefrom.

Then, methanol was added to the filtrate to separate the filtrate into the hexane layer containing unreacted 2-iodobutane and a methanol layer. The thus obtained methanol layer was subjected to evaporation to dryness to obtain 2-(sec-butylamino)phenol as the aimed reaction product.

As a result, it was confirmed that the purity of 2-(sec-butylamino)phenol as produced was 99.2%, the rate of conversion of o-aminophenol was 50%, the selectivity to the N-monoalkylated compound was 100%, and the oxygen absorption initiation time as an index of determining an oxidation-inhibiting property thereof was 300 min.

EXAMPLE 5

Synthesis of 2-(sec-butylamino)phenol

The same procedure as in Example 3 was repeated except for using 120 mL (96 g; 1.2 mol) of methyl ethyl ketone in place of 100 mL of acetone, to conduct the reaction. As a result, it was confirmed that the yield of 2-(sec-butylamino) phenol was 91%, and the oxygen absorption initiation time as an index of determining an oxidation-inhibiting property thereof was 300 min.

EXAMPLE 6

Synthesis of 2-(1-methylpentylamino)phenol

The same procedure as in Example 4 was repeated except for using 2-iodohexane in place of 2-iodobutane, to conduct the reaction. As a result, it was confirmed that the rate of conversion of o-aminophenol was 93%, the selectivity to the N-monoalkylated compound was 41% and the oxygen absorption initiation time as an index of determining an oxidation-inhibiting property thereof was 320 min.

EXAMPLE 7

Synthesis of 2-(1-methylpentylamino)phenol

The same procedure as in Example 6 was repeated except that the molar ratio of 2-iodohexane to o-aminophenol was changed to 0.8, the 2-iodohexane was dropped over 4.5 h, and then the reaction mixture was stirred at room temperature for 0.5 h. As a result, it was confirmed that the rate of conversion of o-aminophenol was 71%, the selectivity to the N-monoalkylated compound was 86%, and the oxygen absorption initiation time as an index of determining an oxidation-inhibiting property thereof was 320 min.

EXAMPLE 8

Synthesis of 2-(1-methylpentylamino)phenol

The same procedure as in Example 3 was repeated except for using 145 mL (121 g; 1.2 mol) of 2-hexanone in place of 100 mL of acetone, to conduct the reaction. As a result, it was confirmed that the rate of conversion of o-aminophenol was 93%, the selectivity to the N-monoalkylated compound (molar ratio of the monoalkylated compound to a sum of the mono- and di-alkylated compounds) was 41%, and the oxygen absorption initiation time as an index of determining an oxidation-inhibiting property thereof was 320 min.

EXAMPLE 9

Synthesis of 3,3'-diamino-4,4'-dihydroxydiphenyl

Into a 200 mL four-necked flask were added 50 mL of dichloromethane and 9 g (48 mmol) of 4,4'-dihydroxydiphenyl, and the contents of the flask were cooled to a temperature of 0° C. or lower. Thereafter, while controlling the reaction temperature in the range of from 0 to 5° C., a 60% by mass nitric acid aqueous solution was dropped into the flask over 2 h. After completion of the dropping, the reaction was further continued for 3 h while controlling the reaction temperature in the range of from 0 to 5° C. After completion of the reaction, 50 mL of water was added to the resultant reaction solution to terminate the reaction.

The obtained reaction solution containing water was neutralized with an aqueous NaOH solution. As a result, it was confirmed that the thus neutralized solution was an orange transparent liquid. The resultant solution was allowed to separate into two layers. The thus separated water layer was acidified with an aqueous hydrochloric acid solution to adjust the pH thereof to 5, thereby obtaining a yellow precipitate. The thus obtained precipitate was mixed with an oil layer previously separated from the water layer, and then DMF was added to the mixture to extract dichloromethane therefrom. As a result, it was confirmed that the yield of the thus obtained 4,4'-dihydroxy-3,3'-dinitrodiphenyl as produced was 96%.

Then, 3 g (10.9 mmol) of the thus obtained 4,4'-dihydroxy-3,3'-dinitrodiphenyl, 0.2 g of Pd/C (Pd content: 5% by mass) and 60 mL of methanol were charged into a 100 mL autoclave, and the contents of the autoclave were heated at 90° C. under a hydrogen pressure of 0.7 MPa. After the elapse of 2 h, the hydrogen absorption was ceased, and the reaction was terminated. After completion of the reaction, 50 mL of tetrahydrofuran (THF) was added to the resultant reaction solution to completely dissolve the reaction product therein. Then, the catalyst was separated from the reaction solution by filtration. Thereafter, the reaction solution was subjected to evaporation to remove methanol and THF therefrom, thereby obtaining the aimed reaction product. As a result, it was confirmed that the oxygen absorption initiation time as an index of determining an oxidation-inhibiting property of the reaction product was 240 min.

EXAMPLE 10

Synthesis of 3,3'-diamino-4,4'-dihydroxydiphenyl

Into a 200 mL four-necked flask were added 50 mL of dichloromethane and 9 g (48 mmol) of 4,4'-dihydroxydiphenyl, and the contents of the flask were cooled to a temperature of 0° C. or lower. Thereafter, while controlling the reaction temperature in the range of from 0 to 5° C., a 60% by mass nitric acid aqueous solution was dropped into the flask over 2 h. After completion of the dropping, the reaction was further continued for 3 h while controlling the reaction temperature in the range of from 0 to 5° C. After completion of the reaction, 50 mL of water was added to the resultant reaction solution to terminate the reaction.

The obtained reaction solution containing water was neutralized with an aqueous NaOH solution. As a result, it was confirmed that the thus neutralized solution was an orange transparent liquid. The resultant solution was allowed to separate into two layers. The thus separated water layer was acidified with an aqueous hydrochloric acid solution to adjust the pH thereof to 5, thereby obtaining a yellow precipitate. The thus obtained precipitate was mixed with an oil layer previously separated from the water layer, and then dichloromethane was distilled off therefrom. The obtained crystallized product was washed with methanol and then dried, thereby obtaining 3,3'-diamino-4,4'-dihydroxydiphenyl. As a result, it was confirmed that the yield of the thus obtained 3,3'-diamino-4,4'-dihydroxydiphenyl was 85%. Then, 10 g (31 mmol) of the thus obtained 3,3'-diamino-4,4'-dihydroxydiphenyl, 0.5 g of Pd/C (Pd content: 5% by mass) and 100 mL of tetrahydrofuran (THF) were charged into a 300 mL autoclave, and the contents of the autoclave were heated at 100° C. under a hydrogen pressure of 1.0 MPa. After the elapse of 1 h, the hydrogen absorption was ceased, and the reaction was terminated.

After completion of the reaction, the reaction mixture was subjected to filtration using a cylindrical filter paper to remove the crystallized product and Pd/C therefrom, and the reaction solution obtained after the filtration was subjected to Soxhlet extraction. After the elapse of 3 h, since the filter cake on the cylindrical filter paper was made of only Pd/C, the Soxhlet extraction was stopped. The obtained reaction solution was cooled, and then the crystallized product was separated therefrom by filtration, thereby obtaining 3,3'-diamino-4,4'-dihydroxydiphenyl. As a result, it was confirmed that the yield of 3,3'-diamino-4,4'-dihydroxydiphenyl was 91%, and the oxygen absorption initiation time as an index of determining an oxidation-inhibiting property thereof was 240 min.

EXAMPLE 11

Synthesis of 2,2-bis(3-amino-4-hydroxyphenyl)propane

The same procedure as in Example 9 was repeated except for using 2,2-bis(4-hydroxyphenyl)propane (bisphenol A) in place of 4,4'-dihydroxydiphenyl, to conduct the reaction. Meanwhile, after completion of the reaction, 50 mL of water was added to the reaction solution to terminate the reaction.

Thereafter, the obtained reaction solution was withdrawn and neutralized with a $NaHCO_3$ solution, and then 50 mL of methanol was added to the neutralized solution.

The obtained methanol solution was concentrated by an evaporator to remove dichloromethane therefrom, thereby precipitating the reaction product. The thus precipitated solid was separated by filtration, washed with methanol and then dried.

It was confirmed that the yield of 2,2-bis(4-hydroxy-3-nitrophenyl)propane was 98%. The thus obtained compound was subjected to hydrogenation reaction by the same method as described in Example 9, thereby obtaining 2,2-bis(3-amino-4-hydroxyphenyl)propane. As a result, it was confirmed that the oxygen absorption initiation time as an index of determining an oxidation-inhibiting property of 2,2-bis(3-amino-4-hydroxyphenyl)propane was 345 min.

EXAMPLE 12

Synthesis of 2,2-bis(3-amino-4-hydroxyphenyl)propane

The same procedure as in Example 10 was repeated except for using 2,2-bis(4-hydroxyphenyl)propane (bisphenol A) in place of 4,4'-dihydroxydiphenyl, to conduct the reaction. Meanwhile, after completion of the reaction, 50 mL of water was added to the reaction solution to terminate the reaction. Thereafter, the obtained reaction solution was withdrawn and neutralized with a $NaHCO_3$ solution, and then 50 mL of methanol was added to the neutralized solution.

The obtained methanol solution was concentrated by an evaporator to remove dichloromethane therefrom, thereby precipitating the reaction product. The thus precipitated solid was separated by filtration, washed with methanol and then dried.

It was confirmed that the yield of 2,2-bis(4-hydroxy-3-nitrophenyl)propane as produced was 90%. The thus obtained compound was subjected to hydrogenation reaction by the same method as described in Example 10, thereby obtaining 2,2-bis(3-amino-4-hydroxyphenyl)propane. As a result, it was confirmed that the oxygen absorption initiation time as an index of determining an oxidation-inhibiting property of 2,2-bis(3-amino-4-hydroxyphenyl)propane was 345 min.

EXAMPLE 13

Synthesis of 4,4'-dihydroxy-3,3'-di(isopropylamino)diphenyl

The same procedure as in Example 1 was repeated except for using 3,3'-diamino-4,4'-dihydroxydiphenyl in place of o-aminophenol. As a result, it was confirmed that the yield of 4,4'-dihydroxy-3,3'-di(isopropylamino)diphenyl as produced was 30%, and the oxygen absorption initiation time as an index of determining an oxidation-inhibiting property thereof was 450 min.

EXAMPLE 14

Synthesis of 4,4'-dihydroxy-3,3'-di(isopropylamino)diphenyl

The same procedure as in Example 3 was repeated except for using 3,3'-diamino-4,4'-dihydroxydiphenyl in place of o-aminophenol. The obtained reaction solution was subjected to suction filtration to remove Pd/C and $MgSO_4$ therefrom. The resultant filtrate was concentrated, and then hexane was added thereto to crystallize a reaction product. The resultant reaction product was dried to obtain 4,4'-dihydroxy-3,3'-di(isopropylamino)diphenyl. As a result, it was confirmed that the yield of 4,4'-dihydroxy-3,3'-di(isopropylamino)diphenyl was 87%, and the oxygen absorption initiation time as an index of determining an oxidation-inhibiting property thereof was 450 min.

EXAMPLE 15

Synthesis of 2,2-bis[3-(isopropylamino)-4-hydroxyphenyl]propane

The same procedure as in Example 1 was repeated except for using 2,2-bis(3-amino-4-hydroxyphenyl)propane in place of o-aminophenol. As a result, it was confirmed that the yield of 2,2-bis[3-(isopropylamino)-4-hydroxyphenyl]propane as produced was 30%, and the oxygen absorption initiation time as an index of determining an oxidation-inhibiting property thereof was 1165 min.

EXAMPLE 16

Synthesis of 2,2-bis[3-(isopropylamino)-4-hydroxyphenyl]propane

The same procedure as in Example 14 was repeated except for using 2,2-bis(3-amino-4-hydroxyphenyl)propane in place of 3,3'-diamino-4,4'-dihydroxydiphenyl. As a result, it was confirmed that the yield of 2,2-bis[3-(isopropylamino)-4-hydroxyphenyl]propane as produced was 92%, and the oxygen absorption initiation time as an index of determining an oxidation-inhibiting property thereof was 1165 min.

EXAMPLE 17

Synthesis of 2,2-bis[3-(sec-butylamino)-4-hydroxyphenyl]propane

The same procedure as in Example 14 was repeated except for using 120 mL of methyl ethyl ketone in place of 100 mL of acetone. As a result, it was confirmed that the yield of 2,2-bis[3-(sec-butylamino)-4-hydroxyphenyl]propane as produced was 91%, and the oxygen absorption initiation time as an index of determining an oxidation-inhibiting property thereof was 790 min.

EXAMPLE 18

Synthesis of 2-(isopropylamino)-4-tert-butylphenol

The same procedure as in Example 3 was repeated except for using 2-amino-4-tert-butylphenol in place of o-aminophenol. As a result, it was confirmed that the yield of 2-(isopropylamino)-4-tert-butylphenol as produced was 89%, and the oxygen absorption initiation time as an index of determining an oxidation-inhibiting property thereof was 700 min.

COMPARATIVE EXAMPLE 1

The oxidation-inhibiting property of the commercially available o-aminophenol was evaluated. As a result, it was confirmed that the oxygen absorption initiation time thereof was 180 min.

COMPARATIVE EXAMPLE 2

The oxidation-inhibiting property of the commercially available 2,6-di-tert-butyl-4-methylphenol (BHT) was evaluated. As a result, it was confirmed that the oxygen absorption initiation time thereof was 180 min.

COMPARATIVE EXAMPLE 3

The oxidation-inhibiting property of the commercially available isopropyl aniline was evaluated. As a result, it was confirmed that the oxygen absorption initiation time thereof was 120 min.

COMPARATIVE EXAMPLE 4

The oxidation-inhibiting property of the commercially available N-isopropyl-N'-phenyl-p-phenylenediamine was evaluated. As a result, it was confirmed that the oxygen absorption initiation time thereof was 160 min.

INDUSTRIAL APPLICABILITY

The antioxidant of the present invention is made of an aromatic hydroxyamine derivative in which a hydroxyl group and an amino or monoalkyl-substituted amino group are respectively bonded to adjacent positions of an aromatic ring thereof, exhibits an excellent oxidation-inhibiting property owing to interaction between the hydroxyl group and the amino group in a molecule thereof, and can be used as an antioxidant for plastic products, rubber products, petroleum products, etc.

Further, the aromatic hydroxyamine derivative can also be used as a polymerization inhibitor.

In addition, the bisaminophenol derivatives of the present invention as novel substances exhibit an extremely excellent oxidation-inhibiting property, and can be more suitably used as an antioxidant or a polymerization inhibitor.

The invention claimed is:

1. A method of using an aromatic hydroxyamine derivative having a structure represented by the general formula (I) as an antioxidant:

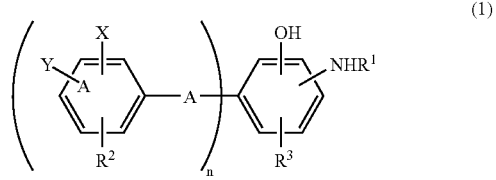

wherein $R^1$, $R^2$ and $R^3$ are each independently a hydrogen atom or an alkyl group having 1 to 20 carbon atoms; X is a hydrogen atom or an OH group; Y is a hydrogen atom or an $NHR^1$ group; A is a direct bond, —O—, —NH—, —$SO_2$—, —$CH_2$— or —$C(CH_3)_2$—, and when an OH group and an $NHR^1$ group are introduced to a unilateral benzene ring, these groups are respectively bonded to adjacent positions of the benzene ring; and n is 0 or 1 with the proviso that when n is 0, $R^1$ is not a hydrogen atom.

2. The method according to claim 1, wherein the antioxidant is used for plastics, rubbers or petroleum products.

3. A method of using a bisaminophenol derivative represented by the general formula (I) as an antioxidant:

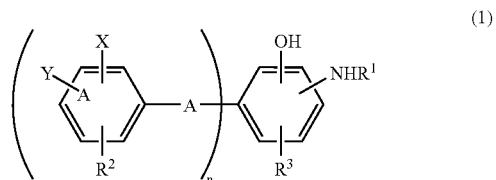

wherein n is 1; $R^2$ and $R^3$ are each a hydrogen atom; X is an OH group; Y is an $NHR^1$ group; A is —$C(CH_3)_2$—; and $R^1$ is isopropyl, isobutyl or isohexyl.

* * * * *